United States Patent
Correra et al.

(10) Patent No.: US 6,642,056 B1
(45) Date of Patent: Nov. 4, 2003

(54) PROCESS FOR DETERMINING THE STABILITY OF ASPHALTENES IN LIVE OIL

(75) Inventors: Sebastiano Correra, S. Donato Milanese (IT); Francesca Donaggio, Milan (IT); Delfina Bersano, Milan (IT)

(73) Assignee: Enitecnologie S.p.A., San Donato Milanese (IT)

(*) Notice: Subject to any disclaimer, the term of this patent is extended or adjusted under 35 U.S.C. 154(b) by 141 days.

(21) Appl. No.: 09/667,792

(22) Filed: Sep. 22, 2000

(30) Foreign Application Priority Data

Sep. 30, 1999 (IT) .................................. MI1999A2032
Oct. 8, 1999 (IT) .................................. MI1999A2105

(51) Int. Cl.[7] .............................................. G01N 33/26
(52) U.S. Cl. ........................ 436/140; 436/60; 436/139; 436/141; 436/142; 436/181; 436/183
(58) Field of Search .................... 436/29, 139, 140, 436/141, 142, 60, 183, 181

(56) References Cited

PUBLICATIONS

R. Risnes et al, Dev. Pet. Sci. 1982, 13, 329–350.*
K. S. Pedersen et al, Fluid Phase Equilibria 1983, 14, 209–218.*
D. C. Lambert et al, 4th UNITAR/UNDP Conference on Heavy Crude and Tar Sands 1988, paper No. 229.*
J. C. Jiang et al, ASC Division of Petrolium Chemistry Preprints 1990, 35, 522–530.*
S. L. Kokal et al, The journal of Canadian Petroleum Technology 1992, 31, 24–30.*
T. N. Chung Report 1992, NIPER–623, order No. DE93000104.*
V. A. Kamath et al, Asphaltene Part. Fossil Fuel Explor., Recovery, Refin., Prod. Processes Symp. 1994, 205–227.*
T. Yang et al, Fluid Phase Equilibria 1997, 128, 183–197.*
J. S. Buckley et al, AlChE Metting Preprint 1997, 61f.*
N. A. Smirnova et al, Fluid Phase Equilibria 1998, 150–151, 161–171.*
Z. Yang et al, Fluid Phase Equilibria 1999, 157, 143–158.*
S. I. Andersen et al, AlChE Metting Preprint 1999, 52a.*
R. Cimino, et al., Proceedings of the International Symposium on Oilfield Chemistry, Society of Petroleum Engineers, pps. 499–512, "Thermodynamic Modelling for Prediction of Asphaltene Deposition in Live Oils," Feb. 14–17, 1995.
A. Hirschberg, et al., Society of Petroleum Engineers Journal, vol. 24, No. 3, pps. 283–293, "Influence of Temperature and Pressure on Asphaltene Flocculation," Jun. 1984.
G. Hotier, et al., Revue De L'institut Francais Du PÉtrole, vol. 38, No. 1, pps. 101–120, "Action De Divers Diluants Sur Les Produits Pétroliers Lourds: Mesure Interprétation ét Prévision De La Floculation Des Asphaltènes," Jan.–Feb. 1983.

* cited by examiner

*Primary Examiner*—Arlen Soderquist
(74) *Attorney, Agent, or Firm*—Oblon, Spivak, McClelland, Maier & Neustadt, P.C.

(57) ABSTRACT

A process is described for determining the stability of asphaltenes in oil fields, which comprises the following steps:

a) titrations of stock tank oil are carried out; the values measured are then used, together with physico-chemical analyses of the stock tank oil, to thermodynamically characterize the asphaltenes and the heavy oil fraction;

b) using the physico-chemical analyses of live oil, the experimental data relating to its phase behavior are interpolated in order to provide a better representation by means of an equation of state;

c) using the equation of state thus calibrated and the characterization of the asphaltenes, the stability of the latter is verified in relation to the temperature and pressure of live oil, using the equation describing the behavior of a sterically stabilized colloid.

6 Claims, 3 Drawing Sheets

PROCESS FOR DETERMINING THE STABILITY OF ASPHALTENES IN LIVE OIL

BACKGROUND OF THE INVENTION

1. Field of the Invention

The present invention relates to a process for deter-mining the stability of asphaltenes in live oil.

2. Description of the Background

Asphaltenes, substances defined on the basis of their insolubility in paraffinic solvents (for example, n-pentane or n-heptane) are present in almost all crude oils. Asphaltenes have a high aromaticity and molecular weight; they also have a greater content of heteroatoms with respect to the corresponding soluble fraction (malthenes).

The structure and chemical behavior of asphaltenes vary a lot in relation to their origin and preparation process; if particular conditions are reached in the field, they can precipitate, blocking the pores and thus causing serious production problems. They can also precipitate along the production string, increasing the pressure drop and thus reducing the well production.

The problem of well-drilling operators is to know the conditions, particularly temperature and pressure, under which asphaltenes are stable in live oil. The term "live oil" refers to crude oil under temperature, pressure, and optionally, dissolved gas conditions, which are encountered in the reservoir, in which the crude oil is present.

In fact, during the extraction of crude oil, it may happen, owing to variations in pressure and temperature, that the asphaltenes present in the oil separate, thus either partially or even totally blocking the crude-oil extraction pipes.

As a result, the well productivity begins to decrease, with evident economic damage.

SUMMARY OF THE INVENTION

The present invention relates to a process for determining the stability of asphaltenes in oil fields.

In this process, use is made of the following equations:

$$(v_s/RT)(\delta_a - \delta_s)^2 = \chi \quad \text{(equation 1)};$$

$$v_s = v_o x_o + v_{gs} x_{gs} + v_p x_p \quad \text{(equation 2)};$$

$$\delta_s = \delta_o \phi_o + \delta_{gs} \phi_{gs} + \delta_p \phi_p \quad \text{(equation 3)};$$

$$\delta_a(T) = \delta_a(T_o) \exp[-9.1 \cdot 10^{-4}(T - T^o)] \quad \text{(equation 4)}.$$

In the above equations $\delta_s$ is the solubility parameter of the "solvent mixture", i.e. of everything but asphaltenes, $\delta_a$ is the solubility parameter of the asphaltenes, $\delta_o$ is the solubility parameter of the oil ($\delta_{sto}$ for stock tank oil and $\delta_{lo}$ for live oil), $\delta_p$ is the solubility parameter of the paraffin used in the titration, $\delta_{gs}$ is the solubility parameter of the good solvent optionally added to the oil, $\chi$ is the asphaltene-solvent mixture interaction parameter, $v_s$ is the molar volume of the "solvent mixture", $v_o$ is the molar volume of the oil ($v_{sto}$ for stock tank oil, $v_{lo}$ for live oil), $v_p$ is the molar volume of the paraffin used in the titration, $v_{gs}$ is the molar volume of the good solvent optionally added to the oil, R is the universal gas constant, T is the temperature in Kelvin degrees, $x_o$ is the molar fraction of the stock oil under threshold conditions, $x_{gs}$ is the molar fraction of the good solvent under threshold conditions, $x_p$ is the molar fraction of the paraffin under threshold conditions, $\phi_o$ is the volumetric fraction of the oil under threshold conditions, $\phi_p$ is the volumetric fraction of the paraffin under threshold conditions, $\phi_{gs}$ is the volumetric fraction of the good solvent under threshold conditions, $T_o$ is the reference temperature, coinciding, from a practical point of view, with the measurement temperature.

The precipitation threshold is defined as the point in which, during the titration, the separation of the asphaltenes begins. The term "titration" means addition to the oil, to which a good solvent has optionally been added, of an asphaltene precipitant n-paraffin (for example n-heptane), until a concentration is reached which induces the precipitation of the asphaltenes.

The term "good solvent" refers to any solvent capable of solvating the asphaltenes, for example aromatic solvents such as toluene; the various titrations are effected by initially adding different quantities of a specific good solvent to the oil.

The term "stock tank oil" means oil under surface conditions (pressure of about 1 atmosphere, temperature of about 25° C., absence of dissolved gases).

The present invention relates to a process for determining the stability of asphaltenes in oil fields, characterized in that it comprises the following steps:

a) titrations are carried out of stock tank oil, diluted with good solvents, with $C_5$–$C_{20}$ aliphatic hydrocarbons, preferably $C_5$–$C_{10}$ paraffins, even more preferably with n-heptane, thus determining the precipitation threshold of the asphaltenes, said threshold being determined at a temperature ranging from 20° C. to the field temperature, preferably the field temperature; subsequently by means of equations (1), with $\chi=0,5$, (2) and (3) (referring stock tank oil), $\delta_{sto}(T)$ and $\delta_a(T)$, are obtained;

b) from the physico-chemical analyses of the stock tank oil and $\delta_{sto}(T)$ determined in step (a), the boiling point of the residue ($T_{bp}$ of the residue) is obtained, by means of an equation of state, preferably the RKS equation (Redlich, Kwong, Soave);

c) from the $T_{bp}$ of the residue determined in (b) and from physico-chemical analyses of the live oil, the experimental data relating to the phase behavior of the live oil are interpolated, in order to improve the representation of the live oil by means of the above equation of state;

d) using the equation of state with the parameters determined in step (c), the $v_{lo}$ and $\delta_{lo}$ values of the live oil are determined under different T and P conditions of interest;

e) the $\chi$ parameter is evaluated for every condition using:

(i) $\delta_a$ referring to the temperature T, this value being equal to that determined in step (a) if the measurement has been effected at the temperature T or, if the measurement in (a) has been effected at a different temperature, calculated from that obtained in (a) by means of equation (4);

(ii) $v_{lo}$ and $\delta_{lo}$ obtained in (d), these parameters being used in equation (1);

f) the stability of the asphaltenes being correlated to the $\chi$ parameter, the asphaltenes are stable when $\chi<0.5$, and unstable when $\chi \geq 0.5$.

The precipitation of the asphaltenes can be interpreted as a precipitation of a sterically stabilized colloid; the precipitation start condition (theta point) is expressed by equation (5):

$$\chi = \chi\theta \quad \text{(equation 5);}$$

wherein $\chi$=the asphaltene-solvent mixture interaction parameter; $\chi\theta=0.5$.

On applying the Bragg-Williams expression to the above equation, expression (6) is reached:

$$(v_s/RT)(\delta_a - \delta_s)^2 = 0.5 \quad \text{(equation 6).}$$

Equation (6) does not have any dependence on the concentration of the starting solution, but makes the precipitation threshold of the asphaltenes depend only on the interaction parameter—i.e. on the difference of the solubility parameters $(\delta_a - \delta_s)$ and on the molar volume of the solvent mixture $v_s$.

This independence of the threshold from the concentration is experimentally confirmed by all determinations described in literature (see for example Hotier G., Robin M. (1983), Revue de l'IFP, 3–8 (1):101); a strong indication of the model capacity is therefore to reproduce the physics of the phenomenon.

Equation (6) was applied to the process of the present invention.

The first step (a) of the present invention consists in a series of titrations of a stock tank oil diluted with good solvents, preferably aromatic, for example toluene, with various $C_5$-$C_{20}$ hydrocarbons, preferably $C_5$-$C_{10}$ paraffins, even more preferably n-heptane. The titrations are carried out at a temperature ranging from 20° C. to the field temperature, preferably the field temperature. A typical example of this titration is indicated in FIG. 1, which shows the absorbance trend in a titration with paraffin of an initially stable solution. Each step of the curve corresponds to the addition of a certain volume of paraffin; when the threshold is reached, the asphaltenes precipitate, strongly increasing the absorbance of the solution. Consequently, when the step is no longer horizontal, threshold conditions prevail. The above threshold is determined by means of absorbance measurements, preferably at a wavelength of 800 nm, with a spectrophotometer (see for example Italian patent application IT-A-MI99A 002105 of Aug. 10, 1999) or by other analytical techniques, for example electrically (see for example Italian patent application IT-A-MI97A 01703 of Aug. 7, 1997).

From the above titrations, which measure the precipitation threshold of asphaltenes, data are obtained which are conveniently indicated in a graph (FIG. 2); the abscissa indicates the good solvent mass/stock tank oil ratio, wherein the threshold precipitant mass/oil mass ratio is indicated in the ordinate. In accordance with literature, this graph is a straight line.

From the titrations described above, the dead oil, paraffin and good solvent masses can be determined, under threshold conditions. If the molecular weights and density of these three components are known, the molar fractions and volumetric fractions appearing in equations (2) and (3) can be easily calculated; whereas for the paraffin and good solvent, the data are available in literature, the molecular weight and density data for the oil are available from routine analysis.

On inserting therefore the above data in equations (2), (3), (4), (6), $\delta_{sto}$ (T), $\delta_a$ (T) are obtained.

In step (b) of the process of the present invention, the boiling point of the residue (residue $T_{bp}$) is obtained. This is made possible by using a state equation in which the physico-chemical data of the stock tank oil $\delta_{sto}$ (T) obtained in step (a), are inserted.

As is known to experts in the field, there are various state equations, among which the most widely used in the oil industry are the RKS (Redich-Kwong-Soave), PR (Pengbinson) and BWR (Benedict-Webb-Rubin) equations; in the case of the hydrocarbon system of interest,) the RKS equation was used.

Using the above state equation and with the help of a calculated program prepared ad hoc, it is possible to obtain $T_{bp}$ of the residue, a parameter which cannot be determined experimentally.

The residue $T_{bp}$ is calculated by assuming that the $\delta_{sto}$ (T) calculated with the RKS equation is equal to the value obtained in step (a).

The third step (c) of the process of the present invention consists in adapting some of the parameters (binary interaction constants) of the state equation in order to reproduce the phase behaviour of the live oil (bubble pressure and field density). This is possible using the experimental data normally obtained in the so-called "PVT report" which is always prepared for each crude oil.

To obtain the best representation of the live oil by means of the RKS equation, a specific calculation program is used.

Step (d) of the process of the present invention consists in calculating $v_{lo}$ and $\delta_{lo}$ i.e. the molar volume and solubility parameter of the live oil, using for this purpose the state equation with the parameters adapted as described in points (b) and (c).

The last step (e) of the process of the present invention consists in verifying the stability of the asphaltenes in the well in relation to the temperature and pressure. This is possible by inserting the $\delta_a$ (T) parameter in equation (1).

The $\delta_{lo}$ and $v_{lo}$ values (lo=live oil) determined in step (d) are inserted in equation (1). An expression is thus obtained whereby it is possible to determine the stability of the asphaltenes in relation to the pressure and temperature.

On effecting this procedure for different temperatures and pressures, it is possible to obtain the phase envelope, corresponding to all the live conditions which make asphaltenes unstable.

An example is provided hereunder of an application in the real case of a crude oil with problems of asphaltene precipitation. In particular, this an Italian paraffinic crude oil (stock tank oil density of 37.8° API).

Using the titration data indicated in (FIG. 2), the solubility parameter of the oil and asphaltenes at the titration temperature were evaluated. On interpolating the experimental results, the following parameter values were obtained:

$$\delta_{sto}(22° \text{C.}) = 19.039 \, [\text{Mpa}^{1/2}]$$

$$\delta_s (22° \text{C.}) = 17.996 \, [\text{Mpa}^{1/2}].$$

The procedure was also carried out at a temperature of 70° C.; on interpolating the $\delta_a$ values thus obtained, its dependency on the temperature was obtained, which proved to be $$\delta_a (T) = \delta_a (T_o) \exp[-5.9 \cdot 10^{-4} (T-T_o)] \quad \text{(equation 7).}$$

For the oil, the molar volume was estimated from the density and average molecular weight. The boiling point of the residue was then calculated by means of a fitting algorithm of the data, in order to reproduce the $\delta_{sto}$ (22° C.) previously calculated.

A wide range of temperatures and pressures were then considered; for each condition (T, P) the $\delta_o$ and $v_o$ values of the liquid phase were calculated, using the SRK equation; as far as the asphaltenes are concerned, the solubility parameter was calculated using expression (7).

For each condition (T, P), the values calculated were used to calculate the first member of equation (1); if it was higher than 0.5, instability conditions prevailed.

The result of the estimation is indicated in FIG. 3, in which a graphic representation is used. It can be observed that the representative point of the field conditions (336.4 bars and 86° C.) are situated in the asphaltene stability zone; on decreasing the pressure, the representative point of the oil conditions moves closer and closer to the instability area, which it reaches in correspondence with about 63° C. and 203 bars.

BRIEF DESCRIPTION OF THE DRAWINGS

This result was then confirmed by the field data.

Figure 1:
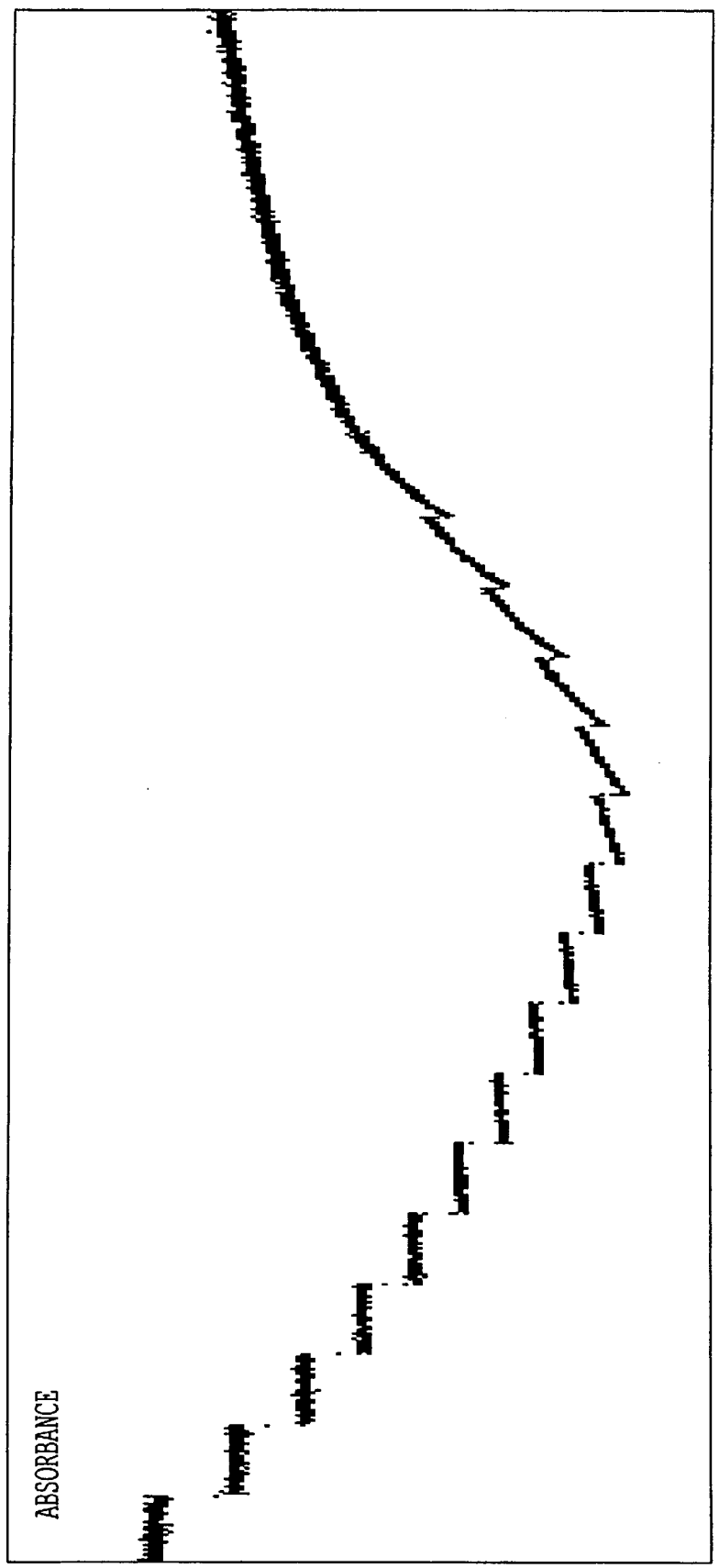
FIG. 1 indicates, in relation to the time, the absorbance measured during a titration with n-heptane of an initially stable solution of a light oil diluted with toluene.
Figure 2:
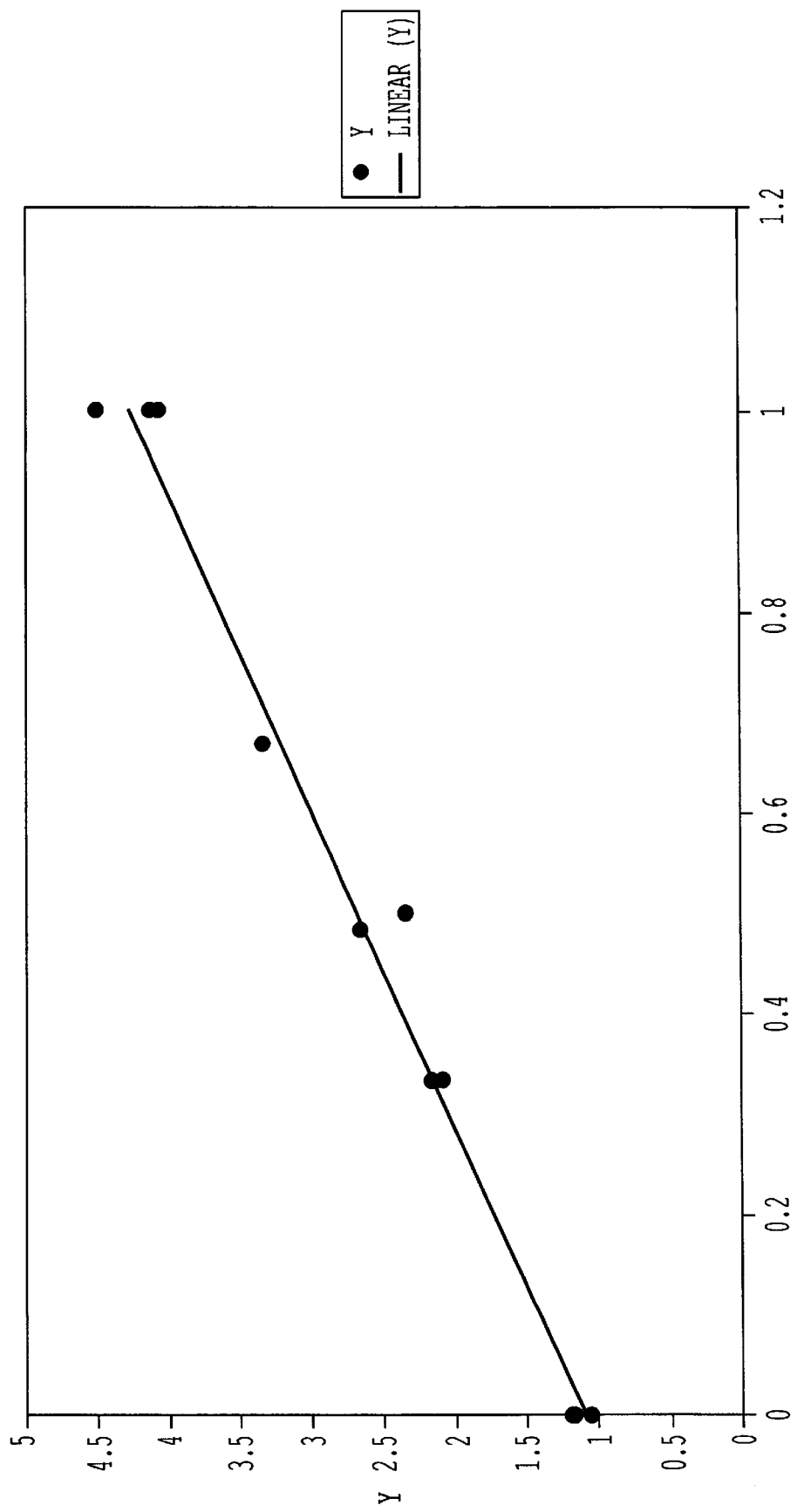
FIG. 2 is a plot of good solvent mass/stock tank oil ratio versus threshold precipitant mass/oil mass ratio.
Figure 3:
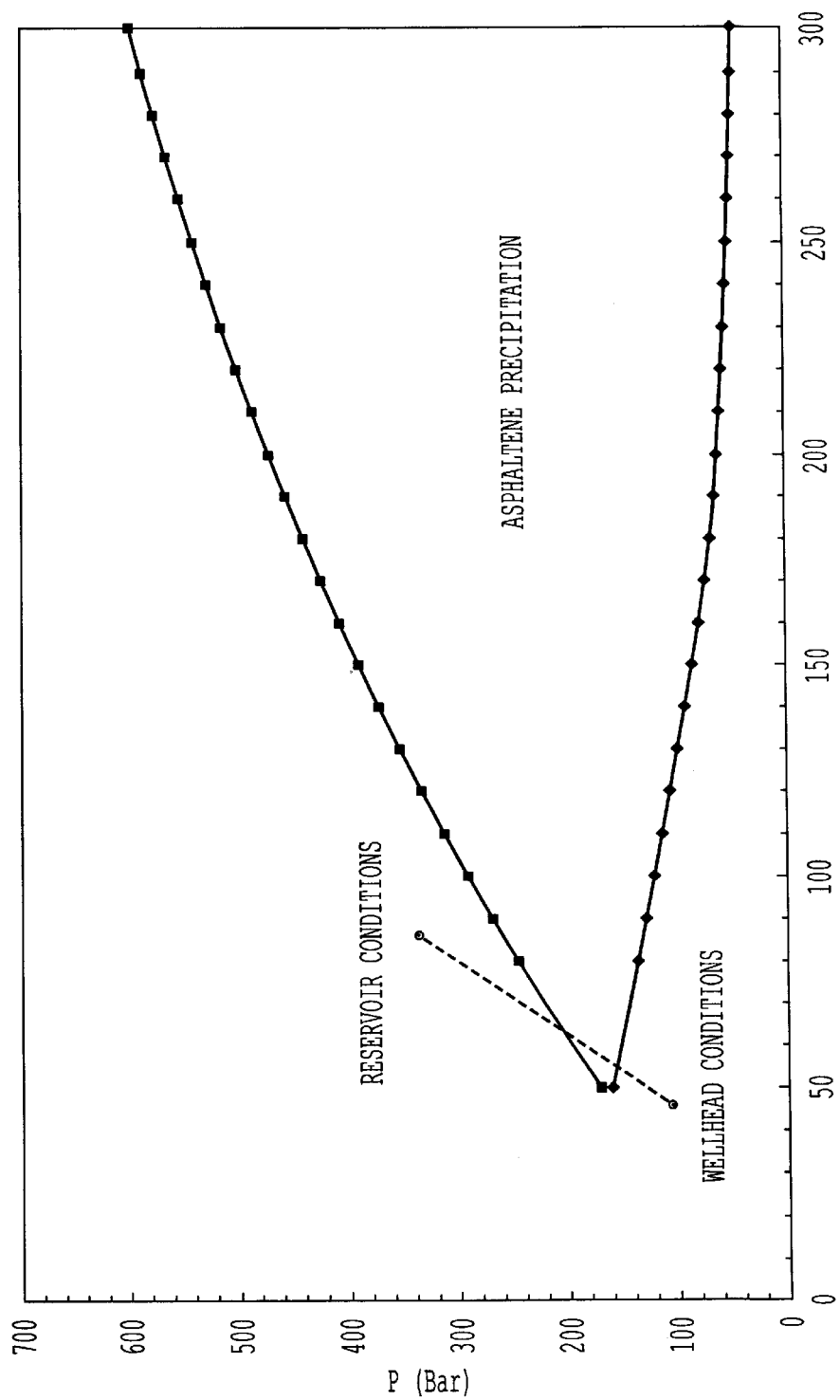
FIG. 3 indicates the stability prediction for a light oil. The model developed allows a (T,P) plane to be subdivided into two zones, one of which the asphaltenes are stable and another in which there is precipitation.

What is claimed is:

1. A process for determining the stability of asphaltenes in oil fields, comprising:

a) titrating a stock tank oil obtained from a live oil, which is diluted with a solvent for the asphaltenes in the tank oil, with a $C_5$-$C_{20}$-aliphatic hydrocarbon titrant at a temperature ranging from 20° C. to the field temperature, thereby determining the precipitation threshold of the asphaltenes present in the tank oil;

a') determining the parameters $\delta_{sto}$ (T) and $\delta_a$ (T) by means of equations (6), (2) and (3):

$$(v_s/RT)(\delta_a-\delta_s)^2=0.5 \quad (6)$$

$$v_s=v_{sto}x_{sto}+v_{gs}x_{gs}+v_px_p \quad (2)$$

$$\delta_s=\delta_{sto}\Phi_{sto}+\delta_{gs}\Phi_{gs}+\delta_p\Phi_p \quad (3)$$

wherein $v_s$ is the molar volume of the mixture of solvent and stock tank oil at the precipitation threshold,
   $v_{sto}$ is the molar volume of the stock tank oil,
   $v_{gs}$ is the molar volume of the solvent,
   $v_p$ is the molar volume of the hydrocarbon titrant,
   $v_s$ is the molar volume of the mixture obtained upon titration but not including the asphaltene component of the stock tank oil,
   $\delta_a$ is the solubility parameter of the asphaltenes,
   $\delta_{sto}$ is the solubility parameter of the stock tank oil,
   $\delta_s$ is the solubility parameter of the mixture obtained upon titration but not including the asphaltene component of the stock tank oil,
   $\delta_p$ is the solubility parameter of the hydrocarbon titrant, and
   $\delta_{gs}$ is the solubility parameter of the solvent,
   $\Phi_{sto}$ is the volumetric fraction of the stock tank oil under threshold conditions,
   $\Phi_p$ is the volumetric fraction of the hydrocarbon titrant under threshold conditions,
   $\Phi_{gs}$ is the volumetric fraction of the solvent under threshold conditions,
   $x_{sto}$ is the molar fraction of the stock tank oil under threshold conditions,
   $x_{gs}$ is the molar fraction of the solvent under threshold conditions,
   $x_p$ is the molar fraction of the hydrocarbon titrant under threshold conditions;

b) determining the boiling point ($T_{bp}$) of the residue obtained from the stock tank oil from the physico-chemical analytical data of the stock tank oil and $\delta_{sto}$ (T) determined in step (a') by means of an equation of state;

c) interpolating the experimental data relating to the phase behavior of the live oil from the $T_{bp}$ of the residue obtained in step (b) and from the physico-chemical analytical data of the live oil, thereby improving the representation of the live oil by means of the equation of state appropriated in step (b);

d) determining the $v_{lo}$ and $\delta_{lo}$ values of the live oil under different T and P conditions of interest employing the equation of state appropriated in step (b);

e) employing equation (1), which is $(v_{lo}/RT)(\delta_a-\delta_{lo})^2=\chi$, determining the value of $\chi$ for every T and P condition of step (d), employing $\delta_a$ determined in step (a) for temperature T or, if a measurement has been calculated from a temperature different from step (a), calculating the temperature by equation (4) which is $\delta_a(T)=\delta_a(T_o)\exp[-9.1\cdot10^{-4}(T-T^o)]$, and by employing $v_{lo}$ and $\delta_{lo}$ determined in step (d); and f) ascertaining the stability of the asphaltenes from the $\chi$ parameters determined, the asphaltenes being stable when $\chi<0.5$ and unstable when $\chi\geq0.5$.

2. The process according to claim 1, wherein the equation of state of step (b) is the RKS (Redlich, Kwong, Soave) equation.

3. The process according to claim 1, wherein the titration of step (a) is employed with a $C_5$–$C_{10}$-paraffin titrant.

4. The process according to claim 3, wherein the titration of step (a) is employed with heptane as the titrant.

5. The process according to claim 1, wherein the titration of step (a) is conducted at a temperature that is essentially the field temperature.

6. The process according to claim 1, wherein the solvent is toluene.

* * * * *